United States Patent [19]

Lormeau et al.

[11] 4,177,262

[45] Dec. 4, 1979

[54] PLASMINOGEN COMPOSITIONS CONTAINING PREACTIVATED PLASMINOGENS WITH OR WITHOUT NATIVE PLASMINOGENS, PROCESS FOR MAKING SAME, PHARMACEUTICAL COMPOSITIONS AND CONTROL OF BLOOD CLOTS

[75] Inventors: Jean-Claude Lormeau, Maromme-la-Maine; Jean Choay, Paris; Jean Goulay, Oissel, all of France

[73] Assignee: Choay S.A., Paris, France

[21] Appl. No.: 785,166

[22] Filed: Apr. 6, 1977

Related U.S. Application Data

[63] Continuation-in-part of Ser. No. 533,631, Dec. 17, 1974, Pat. No. 4,115,551.

[30] Foreign Application Priority Data

Apr. 7, 1976 [FR] France .................................. 76 10143

[51] Int. Cl.² ..................... A61K 35/50; A61K 35/14

[52] U.S. Cl. ................................. 424/105; 424/101
[58] Field of Search ............................ 424/101, 105

[56] References Cited

PUBLICATIONS

Thorsen–Biochem. et Biophysic. Acta, vol. 393, (1975), pp. 55-65.
Chem. Abst. Subject Index (Chemical), vol. 84, (Jan.-Jun. 1976), pp. 3912cs & 3913cs.

*Primary Examiner*—Sam Rosen
*Attorney, Agent, or Firm*—Weiser, Stapler & Spivak

[57] ABSTRACT

The invention pertains to water soluble compositions having plasminogen activity capable of activation to plasmin formed of a mixture of different plasminogen compounds, among which native plasminogen and lysyl-plasminogen. It further concerns such compositions freed from the native plasminogen. They are obtained by the selective fixation of the other plasminogen compounds on fibrin. These compositions are useful for the production of pharmaceutical compositions.

42 Claims, No Drawings

PLASMINOGEN COMPOSITIONS CONTAINING PREACTIVATED PLASMINOGENS WITH OR WITHOUT NATIVE PLASMINOGENS, PROCESS FOR MAKING SAME, PHARMACEUTICAL COMPOSITIONS AND CONTROL OF BLOOD CLOTS

This is a continuation-in-part of pending application Ser. No. 533,631 filed Dec. 17, 1974, now U.S. Pat. No. 4,115,551, entitled "Compounds of the Plasminogen Type and Method for Obtaining Such Compounds from Placental Pulp."

The invention relates to compositions or products based on compounds of the plasminogen type, preferably of human origin, to the medicaments containing these compositions or products, and to a process for producing and for purifying these compositions or products, more particularly from compositions containing compounds of the watersoluble plasminogen type, extracted from placental pulps.

Compositions or products based on compounds of hydrosoluble plasminogens, and more particularly of placental origin, have already been described in the principal patent, corresponding to U.S. Pat. application Ser. No. 533,631 now U.S. Pat. No. 4,115,551, filed Dec. 17, 1974, of which this application is a continuation-in-part. The latter relates also to a process for producing such compositions from placental pulps, the latter being notably produced by mechanical pulping of frozen placentas, thawing the pulp obtained, the thawing being completed in practice when the temperature of the pulp exceeds 1° C., and by separation, preferably at a temperature of the order of 4° C., of the placental blood, notably by centrifugation and recovery of the insoluble pulp. The latter therefore contains notably the placental tissues and the fibrin clots which were present in the placenta.

According to the process described in the said U.S. Pat. No. 4,115,551, the extraction of the compounds of the plasminogen type retained in the pulps proceeds by maceration of the latter in a solution having a pH compatible with holding the extracted plasminogen in a solution, notably comprised between 5 and 10, and preferably at neutral pH, in the presence of an inhibitor of the plasminogen activation, notably of an $\epsilon$-amino acid, the solution obtained, after removal of the residual pulp, then containing compounds of the plasminogen type of the kind concerned. The plasminogen activation inhibitor and a large portion at least of the proteins which accompany the compounds of the plasminogen type in the above-said solution may be removed by conventional methods, notably those which have been mentioned in the said U.S. Pat. No. 4,115,551.

It has just been possible to produce hydrosoluble compositions or products of the plasminogen type, having a plasminogen content higher than 4 CAU/mg (caseinolytic units per mg) and a plasmin content which can be considered as negligible, since it is usually less than 0.04 CAU/mg.

In particular, the plasminogen contents of the compositions currently obtained by performing the process according to the invention of the principal patent application are, when expressed in microkatals, of the order of 2.3–2.6 microkatals.

For convenience it is recalled that an activity of 1 microkatal of plasminogen corresponds to the amount of plasmin obtained from the corresponding amount of plasminogen, after activation of the latter by urokinase, which is capable of hydrolysing one micromole of the methyl ester of N-acetylglycine-L-lysine per second at 37° C. (determination of the esterolytic activity of plasmin on the pH-stat).

Analysis of the compositions such as obtained by the process according to the principal patent application shows that they contain different types of compounds of the plasminogen type. It is found, notably by resorting to electrofocalisation techniques, that they can give rise to 8 protein peaks, with isoelectric points comprised between 6.00 and 8.25. The determination of the $NH_2$-amino-acid terminals of various compounds of the plasminogen type contained in compositions of the kind concerned (notably by resorting to the technique of GROS and LABOUESSE (Europ. J. Biochem., 1969, 7, p. 453) has permitted the observation that they contain high proportions of "preactivated-plasminogens" or "partially" proteolysed derived from the whole plasminogen called "glutamyl-plasminogen", which has the same aminoacid $NH_2$-terminal as the plasminogen of the circulating blood, notably by loss by the latter of at least one peptide fragment including that of its terminal amino-acids, which is constituted by glutamic acid, whose $NH_2$-group is free.

These compounds of the plasminogen type appear to be of the same type as those which appear transiently in the course of the proteolysis of the native plasminogens in plasmin under the action of a plasminogen activator or the plasmin itself, whence the designations "preactivated plasminogens" or "partially proteolysed plasminogens" which have been used to denote the particular compounds of the plasminogen type concerned.

Among these preactivated plasminogens contained in the preparations of the principal patent, there is often noted, in compositions or products of the kind concerned, a predominent presence of peptide chains having a terminal amino-acid with a free —$NH_2$ group, constituted by methionine, which in the following will be denoted by the expression "methionylplasminogens". Thus they may contain, for example, from 40 to 60% of methionyl plasminogens.

As indicated in the principal patent application, the compositions of the type concerned are hydrosoluble. They are also stable, notably on account of their negligible, if not non-existant, content of plasmin.

It has also been found that compositions produced by the process described in the principal patent application, particularly when it is run on an industrial scale, may also contain considerable amounts of other types of preactivated plasminogens, notably compounds of the plasminogen type whose terminal amino-acid which possesses a free -$NH_2$ group is constituted by lysine (lysil-plasminogen).

The present invention relates to compositions still richer in "preactivated plasminogens", more particularly hydrosoluble compositions of which almost the whole of the constituents of the plasminogen type are of the preactivated type, as well as a process for producing them. More particularly again, it relates to compositions of which all the constituents, notably under the experimental conditions which will be described below, are adapted to be fixed completely and stably, on fibrin clots, contrary to "glutamyl-plasminogen" or to the circulating plasminogen, which are only fixed in a small amount on the fibrin under the same conditions and in any case do not remain bound to the fibrin.

The invention relates lastly also to a process for producing such compositions from initial solutions of compounds of the plasminogen type, to the extent that a portion of these constituents of the plasminogen type are in the preactivated condition or can be brought into this condition.

The hydrosoluble composition according to the present invention, essentially formed from compounds of the plasminogen type capable of being activated into plasmin, is characterized in that:

it is essentially free of glutamyl-plasminogen and of plasmin, the above-said compounds are essentially constituted of preactivated zymogens, notably derivatives of glutamyl-plasminogen, through the loss of at least one peptide fragment including that of its terminal amino-acids which is constituted by glutamic acid, whose $NH_2$-group is free, essentially, all of these compounds are capable of being bound to a fibrin clot and remain bound after washing said clot, under the conditions described hereafter, their isoelectric points are higher than 6.7, notably comprised between 7 and 9.

The technique utilized to determine the degree of fixation of the compounds of the plasminogen on the fibrin is an adaptation of that developed by VAIREL (E.G.) Prod. Pharm. 1970, 5, 25, pp. 347–353, for investigating low plasminic activity. The principle is as follows: the clot is formed by recalcification of 0.4 ml of human plasma, at the end of a glass tube. This clot is washed by making it pass through an isotomic chloride solution, until it is no longer lysed, in the presence of plasminogen activator. The clot is then placed in contact, for a certain time with a solution of the plasminogens to be tested. It is then again washed with isotonic chloride solution in order to extract the unbound plasminogen. The presence of bound plasminogen on the fibrin is established by lysing the clot after placing in contact with a plasminogen activator (Urokinase at 20-CTA units/ml (CTA units: standard units of urokinase activity adopted by the Commitee on Thrombolytic Agents, National Heart Institute, U.S.A) or 150 SK units/ml in the proportion of 2 ml per clot).

Preferably, the composition according to the invention is of placental origin.

The invention also relates more particularly to the compositions essentially formed from preactivated plasminogens alone, especially methionyl-plasminogen or to compositions containing lysyl-plasminogen as a principal constituent.

It relates more particularly again to compositions essentially constituted by methionyl-plasminogen, by lysyl plasminogen and possibly also valyl-plasminogen.

The process according to the invention to obtain compositions according to the invention comprising contacting fibrin with a solution essentially free of plasminogen activation inhibitor, preferably of placental origin, and containing compounds of the plasminogen type, of which a portion is preactivated, at a pH comprised between 6 and 9, preferably at neutral pH, at a temperature comprised between 0 and 40° C., notably of the order of +40° C., for a sufficient time to obtain effective binding of the fibrin of most of the content in preactivated plasminogens of said solution, washing the fibrin, preferably with a medium of the type of that in which the above-said compounds of the plasminogen type in the above-said initial solution were previously dissolved, in order to remove unbound proteins, and thereupon eluting said preactivated plasminogens bound on the fibrin, by placing the latter in contact with a solution of a plasminogen activation inhibitor, these preactivated plasminogens then being recoverable or recovered in the purified state by removal of said inhibitors.

The preferred initial solutions applied in the process according to the present invention are constituted by solutions of compounds of the plasminogen type, such as obtained by the application of the process according to the invention of the principal patent application, notably from placental pulps. These compositions, as has been indicated above, contain in fact already considerable proportions of preactivated plasminogens and in addition are practically free of plasmin. Naturally, however, it is self-evident that the initial solutions used may be obtained from other sources of plasminogens, notably the plasmas, it being however then understood that the compounds of the plasminogen type that they contain, notably "glutamyl-plasminogens", have previously been preactivated in part, by processes known in themselves. There have been described in particular purification techniques for plasminogens from such sources, which have the result of leading to partial proteolysis of the initial plasminogen contents of these sources.

As regards the fibrin used, it is advantageously constituted by a fibrin previously freed of any plasmatic contaminant, notably of traces of residual plasminogens, such fibrin being then insensitive to the action of plasminogen activators.

In one preferred embodiment of the process according to the invention, processing is by chromatography over a fibrin column, equilibrated with a buffered solution, preferably of the same nature and of the same composition as the constituent medium of the initial solution containing the plasminogens to be purified, the process consisting then of passing the initial plasminogen solution to be purified through the fibrin column, of then washing the latter with the above-said medium, in the absence of plasminogen, until the effluents no longer contain proteins, the plasminogens bound on the fibrin of the column then being eluted by the passage of a solution containing a plasminogen activation inhibitor.

The fibrin used may be obtained in any manner known in itself, notably by the addition of thrombin to fibrinogen, notably human fibrinogen, or by dissolving this fibrinogen in a plasma and recalcification of this plasma with stirring.

The fibrin obtained is ground, so as to obtain a powder, preferably a fine powder.

This grinding may be carried out by homogenisation of a suspension of fibrin in an isotonic sodium chloride solution (isotonic chloride solution).

Advantageously, the finely ground fibrin obtained is freed from its plasmatic or other contaminants, notably from the residual plasminogen that it can contain, by several washings, of which at least one is with a solution containing plasminogen activation inhibitor. For example, by washing the fibrin with each time, 4 to 6 times its volume of an aqueous solution, of which at least one washing is with an aqueous 0.5 M ε-amino caproic acid solution, a fibrin is obtained which is insensitive to the action of activators, even after incubation for 24 hours in a urokinase solution (notably in the proportion of 500 mg of fibrin per milliliter of a solution containing 20 CTA units of urokinase).

This fibrin is then used to prepare a column which may be equilibrated with a solution buffered to a pH comprised between 6 and 9, preferably of the order of 7, and of which the ionic force is at least equal to 2. Advantageously, recourse is had to a 9 parts per 1000 sodium chloride solution.

Good extraction yields of the preactivated plasminogens contained in a solution such as defined above are obtained if there is provided for the purification of a solution containing 1 mg of compounds of the plasminogen type, a volume of fibrin column of 1 to 6 ml, notably of the order of 4 ml, by adjusting the hourly throughput of the plasminogen solution to be purified through the column to a rate of about 1 to about 100%, preferably of the order of 25 to 50%, for example 25% of the volume of the column.

The plasminogen solution deposited at the top of the column contains advantageously from 1 to 10 microkatals of plasminogen per ml. After passage of this solution through the column, the column is washed with a volume of buffer solution at least equal to the volume of the column, the end of the passage of the unbound proteins in the effluent then being checked, for example by measurement of the optical density in the wavelength zone at 280 nm.

It is noteworthy that the binding of the preactivated plasminogens on the fibrin, and more particularly of the methionyl and lysyl-plasminogens is sufficiently selective and stable under the specified conditions to withstand this washing by the buffer solution.

The elution of the compounds of the plasminogen type fixed on the fibrin can then be effected with a solution of any known plasminogen inhibitor. It is advantageously carried out with a solution having a concentration equal to or greater than 0.005 M, for example 0.05 M of ε-aminocaproic acid in an isotonic chloride solution.

Of course, it is possible to have recourse to other plasminogen activation inhibitors. By way of example, trans-4-amino-methyl-cyclohexane carboxylic acid and para-amino-methylbenzoic acid may be mentioned.

The compounds of the plasminogen type can then be recovered from the eluate, in any manner known in itself, for example, in the said U.S. Pat. No. 4,115,551. The ε-aminocaproic acid can be separated, for example, by dialysis against distilled water, by passage of the solution through a suitable molecular sieve, or by precipitation of the proteins, for example by means of alcohol or of a salt such as ammonium sulfate. Under the preferred conditions, the proteins eluted are precipitated selectively with alcohol in a 35° GL water-alcohol mixture.

The product finally obtained may be freeze-dried.

Starting from a solution of plasminogens of placental origin, such as obtained by the process according to the invention described in the said U.S. Pat. No. 4,115,551, there is thus therefore obtained compositions totally devoid of "glutamyl-plasminogens", having principally methionine or lysine as terminal —NH amino-acids. The isoelectric points of the constituents of the plasminogenic type of the composition obtained are higher than 6.7. They are notably comprised between 7 and 9. The plasminogens are bound selectively and stably on a clot and remain fixed thereon if said clot is subjected to washing with a solution buffered to a neutral pH free of plasminogen activation inhibitors.

According to other preferred embodiments of the invention, it is possible to proceed with the fixing of the compounds of the plasminogen type on the fibrin, to wash the latter, then to elute the retained plasminogens by resorting to tecnhiques other than chromatography. In particularly, it is possible to proceed batchwise; for example, to form a suspension of the fibrin in the solution of the plasminogens to be purified, to separate and then to recover the fibrin retaining the plasminogen when the fixation is terminated, and to wash it, and then to resuspend the fibrin in a solution containing the plasminogen activation inhibitor, and finally to collect the solution containing the desired preactivated plasminogens, after separation of the fibrin, it being understood that the conditions of duration, pH, and temperature, can be within the ranges which have been indicated.

It should be mentioned that methionyl plasminogen and lysyl plasminogen differ from each other only by a few, not more than five, aminoacids. More particularly lysyl plasminogen seems to be derived from methionyl plasminogen as a result of the loss by the latter of a very small peptide fragment formed of the abovesaid few aminoacids, particularly upon prolonged storage of the extracts obtained at some intermediate stage between the starting extraction process of a crude plasminogen extract from the placental pulps according to the process disclosed in the said U.S. Pat. No. 4,115,551 and the final purification step for obtaining a highly purified composition of plasminogen type compounds, or also as a result of the longer duration of each of the process steps when they are operated with large amounts of starting products, when the whole process is run at an industrial scale.

Therefore, the invention also further relates to compositions having plasminogen activity capable of activation to plasmin, which compositions comprise, in addition to a plasminogen whose terminal amino-acid having a free amino group is glutamic acid (native plasminogen), other plasminogens, (preactivated plasminogens), having lower molecular weights, notably by approximately 7000–8000, in a proportion of at least 40% by weight with respect to the total of plasminogen compounds, and differing from the above said native plasminogen by the absence of peptidic chains or fragments including the above said terminal amino-acid, characterized in that said preactivated plasminogen comprises lysyl plasminogen, the latter possibly even forming the major proportion of said preactivated plasminogens.

The invention then also pertains to the stabe, water soluble compositions so obtained, which are substantially free of plasmin, as well as to the pharmaceutical compositions formed therewithin which such plasminogen compositions are associated with a pharmaceutically acceptable vehicle. Particularly the invention pertains to the injectable solutions of such plasminogen compositions.

Other characteristics of the invention will appear also in the course of the description which follows of one embodiment of the process according to the invention, given solely by way of example.

EXAMPLE

1 — Extraction from placentas and purification of compounds of the plasminogen type.

The starting placentas, the membranes and the placental cords, are frozen as early as delivered and stored at −20° C. The placentas are mechanically ground in the frozen condition, into fragments having 1 to 5 mm long edges, then introduced into two volumes of isotonic chloride solution and thawed with stirring. When the temperature of the suspension reaches +6° C., it is centrifuged. The liquid supernatant (placental blood) containing hemoglobin and the plasmatic proteins, but practically devoid of plasminogen, is discarded. The sediment or pulp, constituted by placental tissue and to a smaller extent by fibrin clots, is macerated in two volumes of 0.05 M ε-aminocaproic acid isotonic chloride solution, for two hours at +4° C., then again centrifuged. The compounds of the plasminogen type extracted are found in the supernatant liquid. They are precipitated by the addition of ammonium sulfate in sufficient amount to obtain 40% of final saturation at pH 7.0. The proenzyme contained in the precipitate is then purified by affinity chromatography (according to the method described by Deutsch (D) and Merz (E.T.) Science, 1970, 170., pp. 1095–1096). Aprotinine (Kunitz inhibitor, pancreatic extract, marketed under the name INIPROL) is added at each stage of the purification in order to avoid any degradation of the plasminogen type compounds by proteolysis due to the contaminating plasmin.

Whatever the amount of initial placenta treated (5.50/200 or 1.000 kg), in all cases there are obtained preparations of compounds of the plasminogen type which, in the dry state, have a specific activity of 2.4–2.6 microkatals per milligrams.

Analysis of the terminal $NH_2$-amino acids, according to the technique of Fros and Labouesse already mentioned, enables the presence of high proportions of lysyl-plasminogen and of methionyl-plasminogen, to be observed, the remaining proportions of compound of the plasminogen type being mostly constituted by glutamyl-plasminogen.

A typical compositin is indicated in Table I below:

TABLE I

| Terminal $NH_2$-amino-acid | Amount in % |
|---|---|
| Methionine | 55 |
| Glutamic acid | 25 |
| Lysine | 20 |
| Valine | traces |

2 — Preparation of a fibrin column.

9 g of human fibrinogen are dissolved in 200 ml of human plasma, with stirring for 3 hours. The plasma is then recalcified by the addition of 30 ml of 2% aqueous $CaCl_2$ solution. After coagulation, the clot formed is left for 36 hours at room temperature, in order that the action of the factor XIII carried by the plasma may be complete and ensure better "solidity" of the fibrin. The clot is then cut into fragments, then homogenized in 1800 ml of isotonic chloride solution (in a homogenizer of the ULTRATURAX type, at maximum speed, for 5 minutes. The fibrin particles are then washed on a Büchner successively by 3 l of isotonic chloride solution, 1 l of 0.5 M ε-aminocaproic acid isotonic chloride solution; 1 l of isotonic chloride solution, 1 l of 2 M, NaCl solution, at pH 7.2 and 2 l of isotonic chloride solution. The fibrin thus obtained is devoid of any plasmatic contaminant and insoluble in a 5 M urea solution, In particular, it does not undergo lysis after placing in contact with a plasminogen activator (20 CTA units/ml urokinase or 150 SK units/ml streptokinase in a proportion of 2 ml for 24 hours).

The fibrin thus obtained is then poured into a column of 2.5 cm in diameter over 45 cm height, equilibrated for 48 hours with isotonic chloride solution at pH 7.2 at a flow rate of 8 ml per hour.

3 — Extraction of preactivated plasminogen constituents from the preparation of compounds of the plasminogen type obtained in step 1.

60 mg of the preparation of compounds of the plasminogen type are dissolved in 30 ml of isotonic chloride solution and deposited at the top of the column. The latter is washed in order to remove the unbound proteins with the same isotonic chloride solution until proteins are absent from the effluent, which is checked by measurement of the optical density of successive washing fractions at 280 nm (nanometers).

The bound plasminogen is eluted by isotonic chloride solution containing in addition ε-aminocaproic acid at a concentration of 0.05 M.

The eluted fraction, which represents about 75% of the proteins of the initial preparation, is constituted by a plasminogen mixture having methionine and lysine as terminal, $NH_2$-amino acids, to the exclusion of glutamyl-plasminogens.

By electrofocalisation, it is observed that the fractions contain proteins of isoelectric points 7.07; 7.65; 8.00; 8.12 and 8.75 respectively.

The eluted proteins are then precipitated selectively by the addition of alcohol to the aqueous solution obtained to produce a 35+ GL water alcohol mixture. The product obtained is then freeze-dried.

All preceding operations were carried out at a temperature of about 4° C. except where other temperatures have been explicitly mentioned.

The products obtained are capable of being bound on fibrin clots, notably clots initially devoid of any plasminogen.

It is recalled in fact that fibrin clots totally devoid of plasminogen are not capable of undergoing lysis in the presence of a plasminogen activator, under the conditions which have been mentioned above. It is however observed that these same clots become capable, after their contacting with the abovesaid products, of undergoing this lysis under the action of a plasminogen activator. On the other hand, these same clots, initially devoid of plasminogen, do not become lysable under the above-indicated conditions, after their placing in contact with the plasma containing a native plasminogen, at least under the same conditions as the compounds according to the invention.

Test results are shown in Table II hereafter, in which there have also been indicated the test conditions, in the column headed "nature of the test".

The aprotinine is added when the plasminogen is dissolved in the buffer, in order to avoid degradation of the plasminogen by the contaminating plasmin, as well as the dissolution of the fibrin by this same plasmin.

Test No. 1 shows that the native plasminogen of the plasma does not remain adsorbed on the fibrin formed during coagulation. On the other hand, the plasminogen extracted from the placenta (Test No. 2) remains adsorbed on the fibrin and the amount adsorbed is a function of that placed in contact with the clots (Test No. 2, 3, 4).

The preparations obtained, which contain preactivated plasminogens constituted medicinal active principles which are particularly valuable due to their capability of being completely bound on fibrin clots, contrary to the glutamyl-plasminogens which tend to remain dissolved in the plasma and which in any case do not remain in the clot. The selective binding of plasminogen preparations on fibrin clots, facilitates lysis of these clots, after complete activation and permits better conception of thrombolytic treatments.

Generally, compositions based on plasminogens according to the invention are applied in the treatment of thrombases and pathological deposits of fibrin, notably in the case of the following clinical indications;

(a) acute respiratory distress in newborn and premature infants in which a complete or partial deficit of plasminogen is present, which syndrome is generaly associated with a fibrin deposit in the region of the pulmonary alveoli;

(b) embolisms and venous thromboses;

(c) micro-embolisms, essentially cerebral;

(d) acute, sub-acute and chronic with tendency to spread, localized and disseminated intravascular coagulations.

For example, the administration of the placental plasminogen may be carried out in continuous venous perfusions, at the rate of 1,000 to 1,200 CAU spread over a period of 24 to 36 hours, or by slow intravenous injections (for a man of 60 kg average weight).

For nursing infants, there can be used doses of 200 CAU every six hours, administered by slow perfusion, in 9/1000 isotonic chloride solution, buffered to pH 7.4 for 24 hours. Preferred administrative forms of the preparations according to the invention include plasminogen solutions in a pharmaceutically acceptable vehicle, notably a physiological serum, preferably glucose.

TABLE II

Study of the fixing of the plasminogens on fibrin

| Test No | Nature of the test | Activator | Result after 24 hours |
|---|---|---|---|
| 1 | Clot washed. Conact with 2 ml of plasma. | Urokinase | no lysis |
|  |  | Streptokinase | no lysis |
| 2 | Clot washed. Contact with 2 ml of buffer containing 0.5 mg/ml of plasminogen according to the invention + 10 µg/ml of aprotinine-washing Duration of contact: 45 minutes. | Urokinase | 100% lysis |
|  |  | Streptokinase | 100% lysis |
| 3 | Test identical with No 2 but with 0.1 mg/ml of plasminogen according to the invention. | Urokinase | 20% lysis |
|  |  | Streptokinase | 20% lysis |
| 4 | Test identical with No 2 but with 0.25 mg/ml of plasminogen according to the invention. | Urokinase | 50% lysis |
|  |  | Streptokinase | 50% lysis |

We claim:

1. A water-soluble biological composition which has plasminogen activity capable of activation to plasmin, which composition is essentially free of plasmin and which comprises: native plasminogen, which native plasminogen is amino-terminal glutamic acid and a preactivated plasminogen, said preactivated plasminogen having a lower molecular weight than the native plasminogen and differing from the native plasminogen by the absence of a peptide fragment which fragment includes said terminal amino acid, said preactivated plasminogen being present in a proportion of at least about 40% by weight of the total plasminogens, and said preactivated plasminogen comprising lysyl plasminogen.

2. The biological composition of claim 1 wherein the preactivated plasminogen has a molecular weight lower than native plasminogen by about 7000 to about 8000.

3. The pharmaceutical composition which comprises the composition of claim 1 and a pharmaceutically acceptable carrier.

4. The composition of claim 1 wherein the major proportion of said preactivated plasminogen is lysyl plasminogen.

5. The pharmaceutical composition which comprises the composition of claim 4 and a pharmaceutically acceptable carrier.

6. A water-soluble biological composition which has plasminogen activity capable of activation to plasmin, which composition is essentially free of plasmin and essentially free of glutamyl-plasminogen, which composition has its isoelectric points higher than 6.7, and comprises water-soluble preactivated plasminogens, having principally methionine or lysine as the terminal $-NH_2$ aminoacids, derived from glutamyl-plasminogen by its loss of a peptide fragment, which fragment includes amino-terminal glutamic acid, and which composition is capable of being fixed essentially in its entirety on a fibrin clot and to remain so fixed after washing with a solution buffered to a neutral pH.

7. The composition of claim 6 whose isoelectric points are in the range of about 7 and 9.

8. The composition of claim 6 which is of placental origin.

9. The composition of claim 6 which comprises methionyl-plasminogen.

10. The composition of claim 6 which comprises lysyl-plasminogen.

11. The composition of claim 6 which comprises methionyl-plasminogen and lysyl-plasminogen.

12. The composition of claim 6 which is constituted essentially of methionyl-plasminogen and lysyl-plasminogen.

13. The process for producing the composition of claim 6 which comprises contacting with fibrin, at a pH in the range of about 6 to about 9 and at a temperature of about 0° to 40° C., a starting solution essentially free of plasminogen activation inhibitor and containing compounds of the plasminogen type of which a portion is preactivated, for a sufficient time for binding of the preactivated plasminogens of said solution on the fibrin, washing the fibrin to remove unbound proteins, and eluting said preactivated plasminogens bound on the fibrin by contacting the fibrin with a solution of plasminogen activation inhibitor.

14. The process of claim 13 wherein the fibrin used is constituted by a fibrin freed of plasma contaminants and insensitive to the action of plasminogen activators.

15. The process of claim 13 which comprises the step of removing the plasminogen activation inhibitor, thereby recovering the preactivated plasminogens free of glutamyl-plasminogen.

16. The process of claim 13 wherein the compounds of the plasminogen type are of placental origin.

17. The process of claim 13 wherein the temperature at which the contacting is performed is about 4° C.

18. The process of claim 13 wherein the contacting is performed at a pH of about neutral.

19. The process of claim 13 wherein said washing of the fibrin to remove unbound proteins is with a solution in which the plasminogens are dissolved in the starting solution.

20. The process of claim 14 wherein the fibrin is free of residual plasminogens.

21. The process of claim 13 wherein the process is carried out by chromatography on a fibrin column.

22. The process of claim 21 wherein prior to said contacting, the chromatography fibrin column is equilibrated with a buffered solution of the same nature and of the same composition as that of the starting solution of the plasminogens to be purified, after said contacting the column is washed with a buffered solution and after said washing the fixed plasminogens are eluted by passage of a solution of a plasminogen activation inhibitor over the fibrin column.

23. The process of claim 22 wherein the buffered solution has an ionic force at least equal to about 2.

24. The process of claim 22 wherein the amount of fibrin used is between about 1 and about 6 mg of fibrin per milligram of plasminogen to be purified.

25. The process of claim 22 wherein the solution containing the plasminogens to be purified is passed through said column at an hourly flow rate between about 1% and 100% by volume per volume of fibrin in the column.

26. The process of claim 22 wherein the elution of the plasminogen bound on the fibrin is carried out by a solution of a plasminogen activation inhibitor whose concentration is equal to or greater than about 0.005 M.

27. The process of claim 13 wherein there is formed a suspension of fibrin in the starting solution containing the plasminogens, the fibrin binding the plasminogen is then separated and the fibrin is washed, is resuspended in a solution containing the plasminogen activation inhibitor, and the solution containing the desired preactivated plasminogens is collected after separation of the fibrin.

28. A pharmaceutical composition comprising the biological composition of claim 6 and a pharmaceutically acceptable carrier.

29. A pharmaceutical composition comprising the biological composition of claim 8 and a pharmaceutically acceptable carrier.

30. A pharmaceutical composition comprising the biological composition of claim 9 and a pharmaceutically acceptable carrier.

31. A pharmaceutical composition comprising the biological composition of claim 10 and a pharmaceutically acceptable carrier.

32. A pharmaceutical composition comprising the biological composition of claim 11 and a pharmaceutically acceptable carrier.

33. A pharmaceutical composition comprising the biological composition of claim 12 and a pharmaceutically acceptable carrier.

34. The composition of claim 6 which is freeze-dried.

35. The composition of claim 28 wherein the carrier is a physiological serum.

36. The composition of claim 35 wherein said serum is a glucose serum.

37. A method of treating thromboses and pathological deposits of fibrin which comprises administering the pharmaceutical composition of claim 28 to the patient, causing the binding of the plasminogen onto the fibrin clots and then causing lysis of clots by administration of a plasminogen activator.

38. A method of treating thromboses and pathological deposits of fibrin which comprises administering the pharmaceutical composition of claim 30 to the patient, causing the binding of the plasminogen onto the fibrin clots and then causing lysis of clots by administration of a plasminogen activator.

39. A method of treating thromboses and pathological deposits of fibrin which comprises administering the pharmaceutical composition of claim 31 to the patient, causing the binding of the plasminogen onto the fibrin clots and then causing lysis of clots by administration of a plasminogen activator.

40. A method of treating thromboses and pathological deposits of fibrin which comprises administering the pharmaceutical composition of claim 32 to the patient, causing the binding of the plasminogen onto the fibrin clots and then causing lysis of clots by administration of a plasminogen activator.

41. A method of treating thromboses and pathological deposits of fibrin which comprises administering the pharmaceutical composition of claim 33 to the patient, causing the binding of the plasminogen onto the fibrin clots and then causing lysis of clots by administration of a plasminogen activator.

42. The method of claim 37 wherein the activator administered is urokinase.

* * * * *